United States Patent [19]
Lehman

[11] Patent Number: 5,390,668
[45] Date of Patent: Feb. 21, 1995

[54] DISPOSABLE MULTITEST BACTERIA FILTER

[75] Inventor: Arlin Lehman, Louisville, Colo.

[73] Assignee: Pulmonary Data Service Instrumentation, Inc., Louisville, Colo.

[21] Appl. No.: 81,786

[22] Filed: Jun. 22, 1993

[51] Int. Cl.$^6$ .............................................. A61B 5/08
[52] U.S. Cl. ............................. 128/205.27; 128/716; 128/719; 96/108
[58] Field of Search .................. 128/201.13, 205.12, 128/205.13, 205.27, 205.29, 716, 719; 165/119; 55/97, DIG. 31, DIG. 35, DIG. 42, DIG. 43, DIG. 49, DIG. 45; 96/108, 152, 189

[56] References Cited

U.S. PATENT DOCUMENTS

| | | | |
|---|---|---|---|
| 4,090,513 | 5/1978 | Togawa | 128/201.13 |
| 4,234,326 | 11/1980 | Bailey et al. | 96/154 |
| 5,035,236 | 7/1991 | Kanegaonkar | 128/201.13 |

FOREIGN PATENT DOCUMENTS

| | | | |
|---|---|---|---|
| 2231509 | 11/1990 | United Kingdom | 128/201.13 |
| 9207601 | 5/1992 | WIPO | 128/201.13 |

Primary Examiner—Edgar S. Burr
Assistant Examiner—Eric P. Raciti
Attorney, Agent, or Firm—Rick Martin

[57] ABSTRACT

A one piece disposable bacteria/virus filter is suited for all lung tests. The 3½" outside diameter embodiment has a low 70 cc dead space and a low 0.60 mm $H_2O$/liter/second airflow at 12 liters per second. The 4" outside diameter embodiment has a low 70 cc dead space and a low 0.45 cm $H_2O$/liter/second airflow at 12 liters per second. Each embodiment has two plastic body halves; each having fins or pins or crosshairs to support the central area of the Filtrete® internal filter mounted therebetween.

18 Claims, 13 Drawing Sheets

DISPOSABLE MULTITEST BACTERIA FILTER

CROSS REFERENCE PATENTS

Co-pending U.S. application Ser. No. 07/929,817 is related and incorporated herein by reference.

FIELD OF THE INVENTION

The present invention relates to disposable bacteria filters especially suitable for spirometers, ventilators and related respiratory apparatus, wherein a single disposable module can meet both the low filter resistance and low dead space requirements of lung testing.

BACKGROUND OF THE INVENTION

Spirometry is the art of determining the health and capacity of the lungs. Original instruments comprised a mouthpiece, blowtube, water cylinder, ballast and chart recorder. The patient blew into the mouthpiece, thereby lifting the ballast a measurable height for a measurable time. Time versus displacement graphs could be combined with the patient's age, weight and medical history to help diagnose lung diseases.

In the past few years the use of computers for spirometry measurement has become commonplace. As a consequence the American Thoracic Society (ATS) publishes and updates a Standardization of Spirometry for spirometry systems including the disposable mouthpiece.

Modern health care facilities perform countless Spirometry tests annually. Spirometers can be the cause of spreading bacteria and viruses resulting in the spread of serious diseases including TB and HIV. Cleansing reusable mouthpieces and instrument parts is a costly and risky procedure. This is especially true considering the control procedures necessary for monitoring compliance of numerous test personnel working under time pressure.

The result of the undesirability of cleansing reusable mouthpieces and instrument parts has led to the development of several disposable mouthpiece designs. Before discussing the development of disposable mouthpieces we must first review some testing basics.

There are three basic tests performed by spirometers. They are first a forced vital capacity test, second a diffusion test, and third a lung volume test. Spirometers used in the office of a physician generally perform only the vital capacity test while the instruments used by a hospital or pulmonary physician are usually capable of performing all three tests. These instruments which perform all three tests are sometimes called total lung analyzers, but they are actually spirometers.

The forced vital capacity test simply measures time versus flow. Low filter resistance is required to assure accurate flow readings. The diffusion test measures the efficiency of oxygen transfer from the alveoli to the blood. This test uses minute amounts of carbon monoxide breathed into the lungs through a closed loop spirometry system. This test requires low dead space in the filter apparatus to assure accurate readings of minute amounts of carbon monoxide. Finally the lung volume test uses a small amount of helium in a closed loop system to measure the lungs residual air after expiration. This test also requires a leak proof seal in the filter apparatus to prevent leakage of helium.

Thus these three tests require different characteristics from the filter apparatus. These ideal characteristics are:

1) Low filter resistance
2) High filtration efficiency of bacteria
3) Low dead space
4) Leak proof seal Further economic and environmental characteristics of the ideal filter are:

5) Low cost
6) Universal mounting capabilities on dozens of spirometers
7) Reduced volumetric disposal of plastics It should be noted that low filter resistance is most easily obtained by having a large dead space and a wide area for gas flow through the filter. Also a minimal filtration efficiency offers a low filter resistance.

Two main disposable filter systems comprise the prior art. First the Pall Barrier Filter TM uses a baffle type barrier which is 99.9% effective in filtering particulate matter including spit. But the barrier is noneffective on airborn bacteria on the order of 0.2 microns. The Pall TM filter has a very low resistance around 0.4 cm $H_2O$/liter/second at 12 liters per second flow. The ATS standard for the total spirometry instrument is less than 1.5 cm $H_2O$/liter/second at 12 liters per second flow. The internal dead space of the Pall TM filter is very low at 40 cc. The cost is quite high at $5 per unit. In summary the Pall TM filter fails to block airborn bacteria (ATS specs do not specify a standard) and is expensive.

The second known disposable filter is the Marquest TM filter. It uses a 3M ® gauze filter named Filtrete ® at a thickness of 200 gm/sq.m. It is 99.99% efficient in filtering airborn bacteria and 99.98% efficient for viruses. Thus, the Marqueste TM filter efficiently filters bacteria and viruses. However, in order to obtain a resistance of about 0.9 cm $H_2O$/liter/second at 12 liters per second flow, Marquest TM creates a large 3½" diameter orifice, thus a large surface area for the Filtrete ®, thereby creating about 150 cc's of dead space. ATS calls for less than 150 cc's of dead space for the total spirometer. Thus, the Marquest TM filter is not suitable for either the diffusion test or the lung volume test. The price, however, at $3.50 per unit is quite an advantage over the Pall TM filter.

Another embodiment of the Filtrete ® filter uses too thin a gauge of Filtrete ® spread across a 2" diameter orifice. This approach creates an acceptably low dead space but an unacceptably high resistance. The filtration efficiency is also reduced. The cost is very low at $1.00 per unit. Thus, this embodiment does not satisfy the market demands.

The present invention uses new support means inside the housing of a one piece disposable bacteria filter. The new support means include fins or posts to support the flexible Filtrete ® filter toward the center. A very low filter resistance can be obtained while simultaneously achieving a low dead space. The following market demands are met:

1) low filter resistance at 0.45-0.60 cm $H_2O$/liter/second at 12 liters per second flow.
2) 99.99% and 99.98% efficient in stopping airborn bacteria and viruses respectively.
3) Low dead space ranging from 70 to 115 cc's.
4) Leak proof design.
5) Low cost at $2.50 per unit.
6) Universal mounting adapters.
7) One disposable bacteria filter can be used for all tests, thus reducing inventory costs.

SUMMARY OF THE INVENTION

The primary object of the present invention is to provide a one piece disposable bacteria/virus filter having low filter resistance and low dead space.

Another object of the present invention is to provide this filter with an internal support means to support a Filtrete ® filter toward its center.

Another object of the present invention is to provide this filter with a universal mounting adapter.

Another object of the present invention is to offer a large 4 inch embodiment having a resistance as low as 0.45 cm $H_2O$/liter/second at 12 liters per second flow and 70 cc's of dead space.

Another object of the present invention is to provide this filter with a leak proof design.

A final object of the present invention is to provide this filter with a low cost basis.

Other objects of this invention will appear from the following description and appended claims, reference being had to the accompanying drawings forming a part of this specification wherein like reference characters designate corresponding parts in the several views.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DETAILED DESCRIPTION OF THE PREFERRED EMBODIMENT

Figure 1:
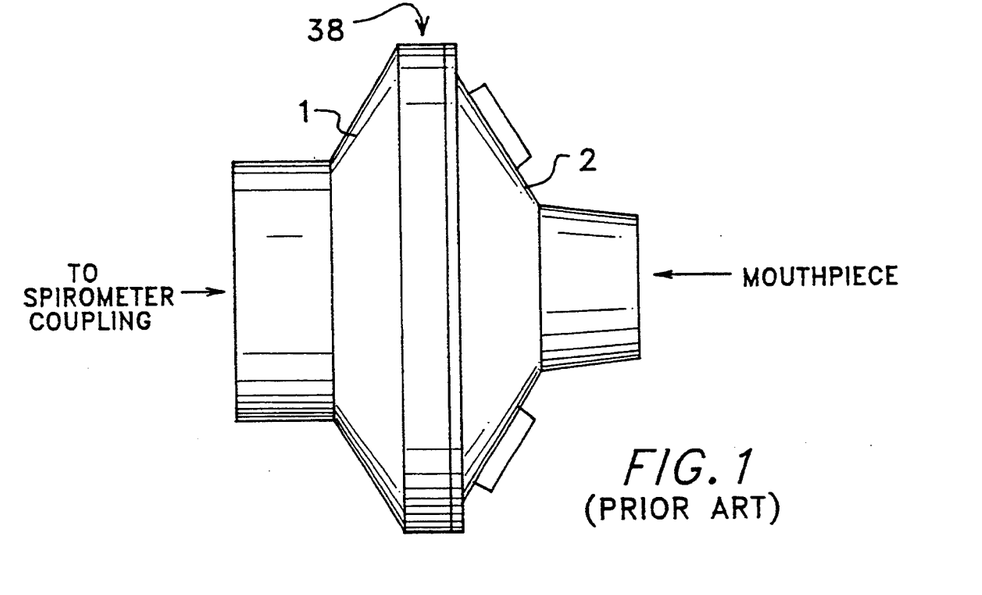
FIG. 1 is a side plan view of a disposable bacteria filter (prior art).
Figure 2:
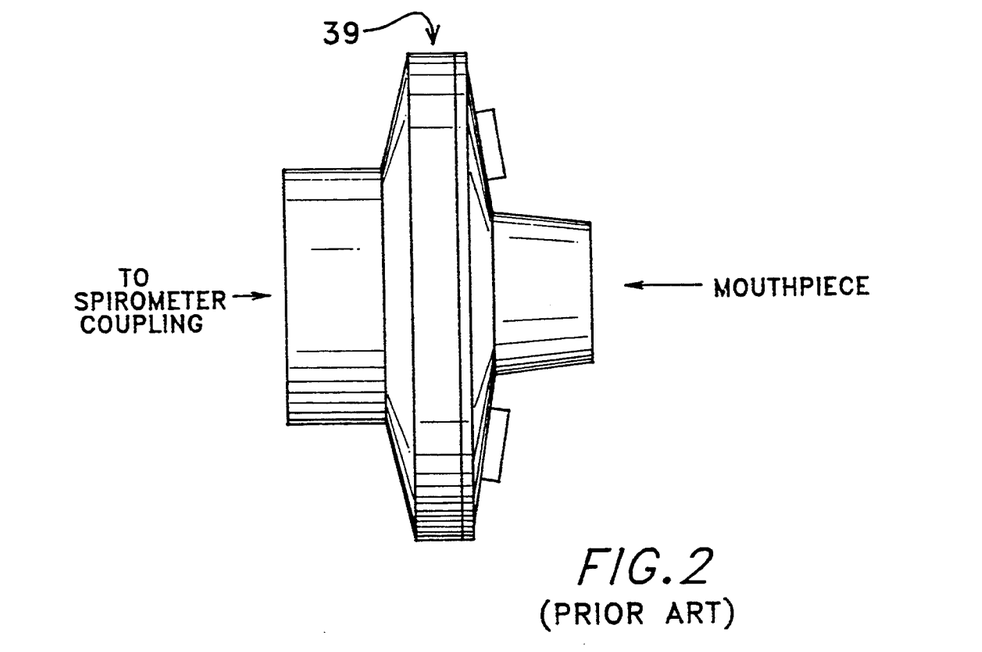
FIG. 2 is a side plan view of a disposable bacteria filter (prior art).

FIGS. 1-5 (a),(b),(c) show a disposable bacteria filter indicative of the prior art. These disposable bacteria filters are available in two designs. FIG. 1 shows a low filter resistance high dead space design disposable bacteria filter 38. FIG. 2 shows a high filter resistance low dead space design disposable bacteria filter 39. These disposable bacteria filters 38, 39 are used in conjunction with a spirometer (not shown) which senses a patients respiratory parameters and sends these parameters to a computer (not shown) for diagnostic analysis.

Figure 3:
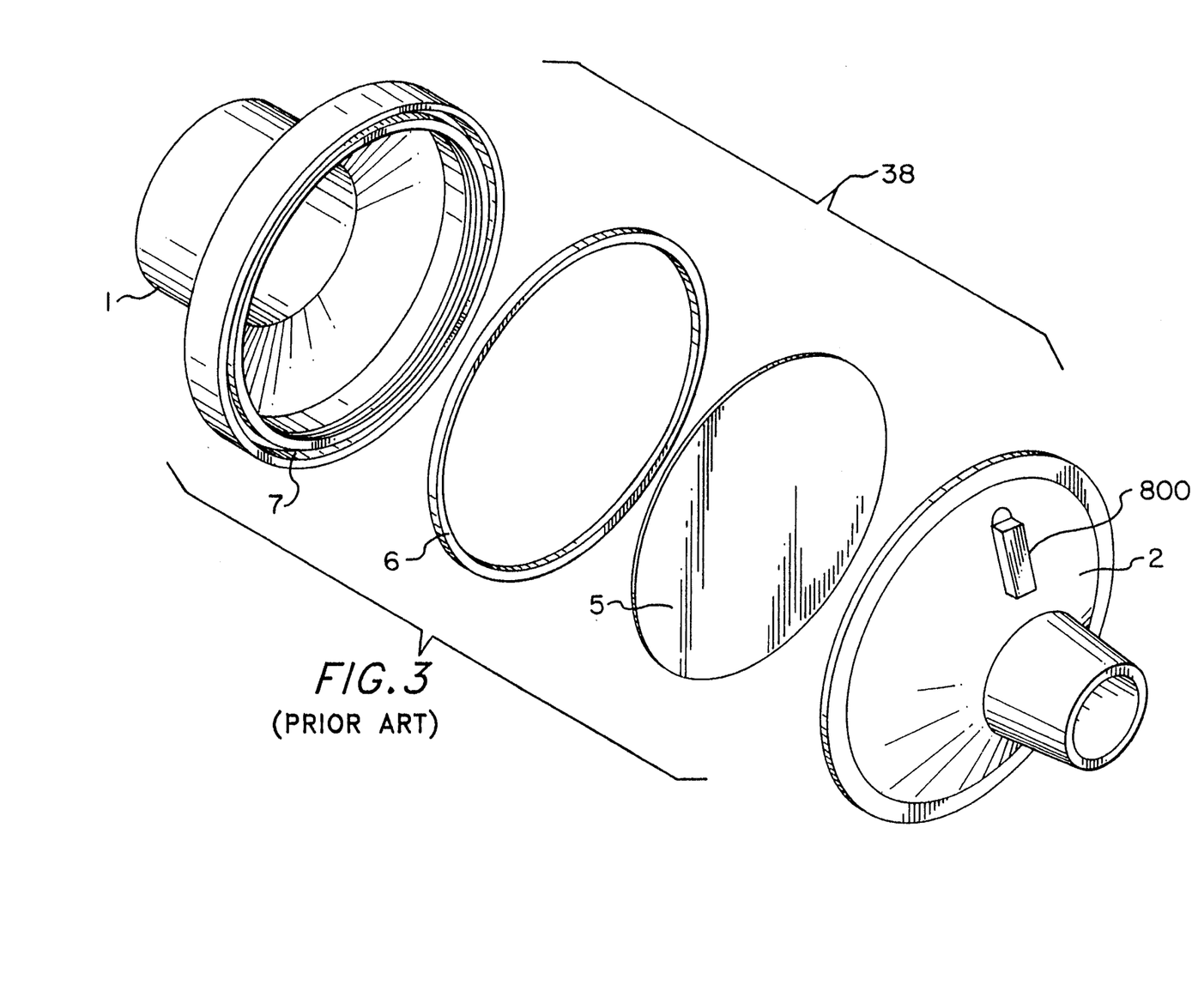
FIG. 3 is an exploded view of the disposable bacteria filter shown in FIG. 1 (prior art).

FIG. 3 shows the components of the disposable bacteria filter 38. This device consists of a mouthpiece 2, a filter means 5, a receptive housing 1 and an O ring 6. Infiltration of external air is prevented by the 0 ring 6 when placed in the recessed groove 7 of the receptive housing 1.

Figure 4A:
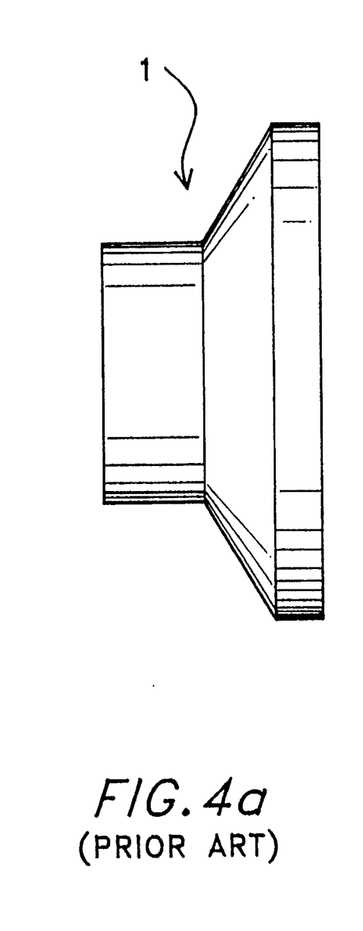
FIG. 4(a) is a side plan view of the receptive housing of the disposable bacteria filter shown in FIG. 1 (prior art).
Figure 4B:
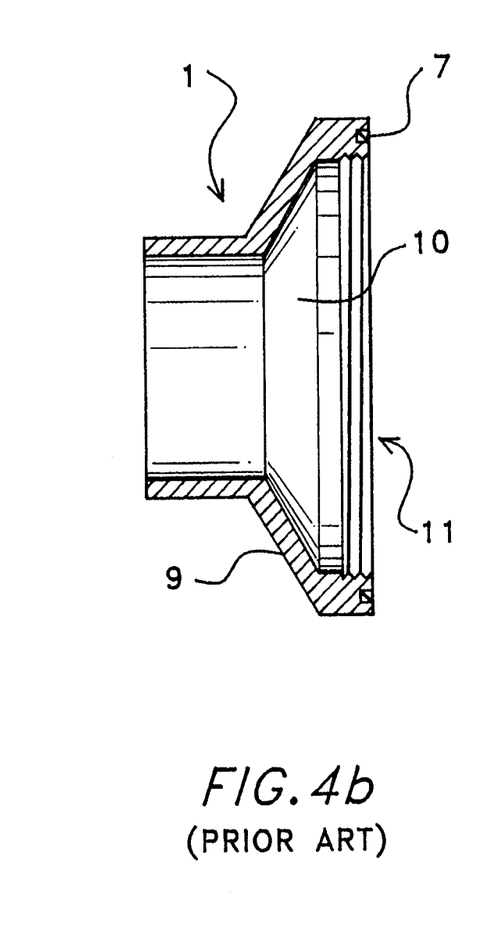
FIG. 4(b) is a cross sectional view of the receptive housing of the disposable bacteria filter shown in FIG. 4(a) (prior art).
Figure 4C:
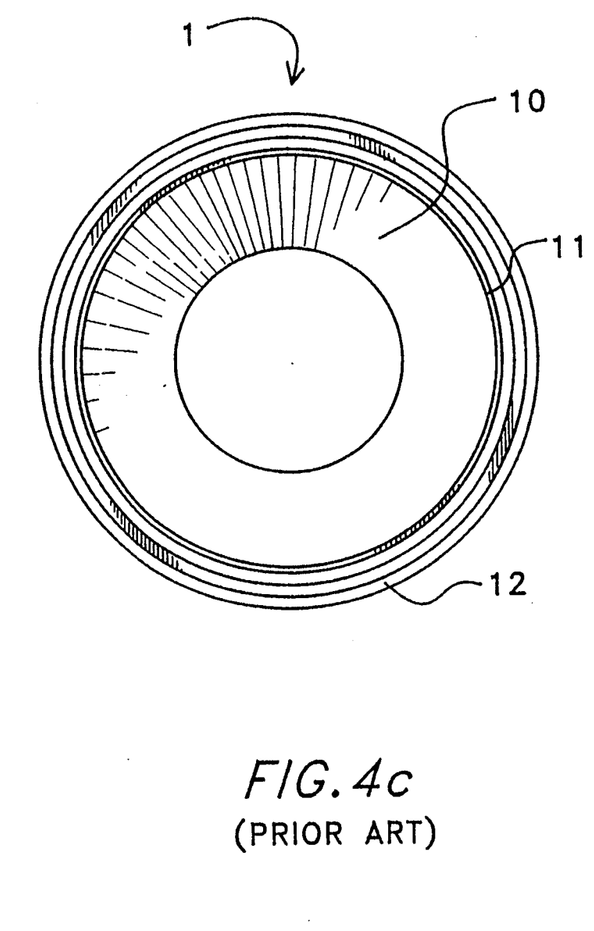
FIG. 4(c) is a front plan view of the receptive housing of the disposable bacteria filter shown in FIG. 4(a) (prior art).
Figure 5A:
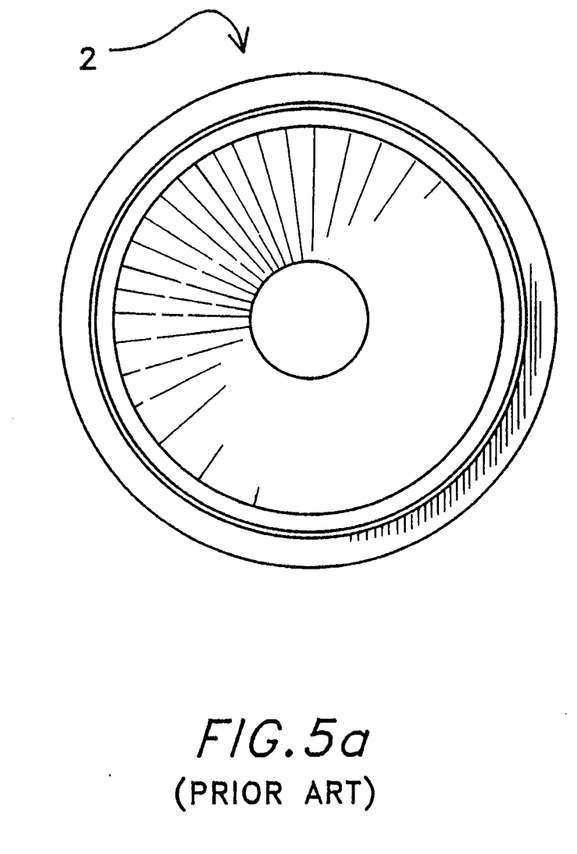
FIG. 5(a) is a front plan view of the mouthpiece housing of the disposable bacteria filter shown in FIG. 1 (prior art).
Figure 5B:
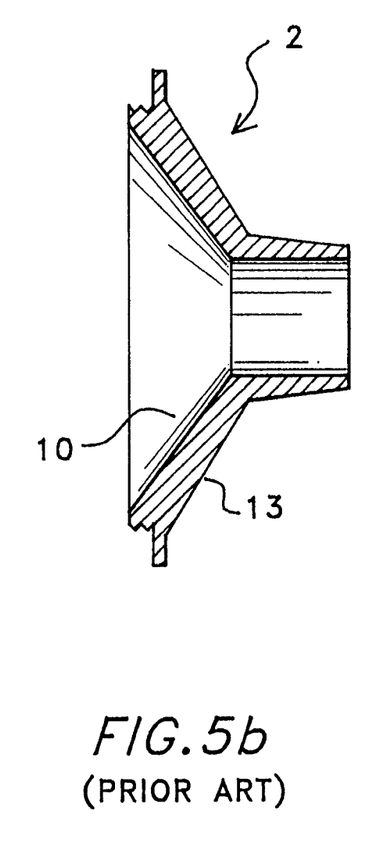
FIG. 5(b) is a cross sectional view of the mouthpiece housing of the disposable bacteria filter shown in FIG. 5(a) (prior art).
Figure 5C:
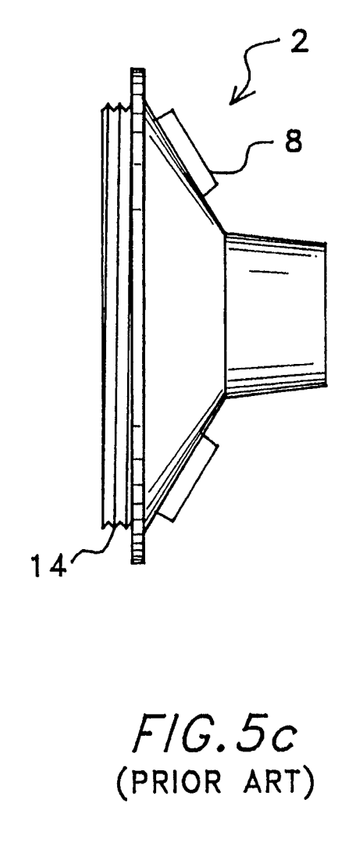
FIG. 5(c) is a side plan view of the mouthpiece housing of the disposable bacteria filter shown in FIG. 5(a) (prior art).
Figure 6:
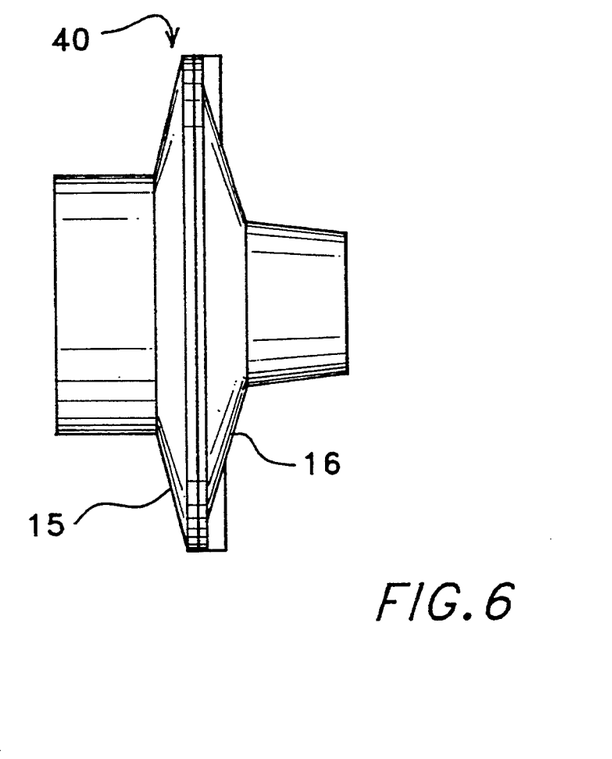
FIG. 6 is a side plan view of a 3½" one piece disposable bacteria filter.

Details of the prior art are shown in FIGS. 4 (a),(b),(c), 5 (a),(b),(c). The O ring 6 (shown in FIG. 3) is placed in the recessed groove 7. A filter means 5 is inserted in the receptive housing unit 1. The female threads 11 of the receptive housing unit 1 are to receive the male threads 14 of the mouthpiece 2. The flange 9 of the receptive housing unit 1 and the flange 13 of the mouthpiece housing unit 2 are designed to provide the desired characteristics of low filter resistance, high filtration, and low dead space 10. Finger tabs 800 are to assist in joining the two housing units.

The patient breathes into the mouthpiece 2 to activate the system.

The filter means 5 must prevent over 99% of airborn bacteria and viruses from passing through the filter. The best known material for filter means 5 is a fibrous pad made by 3M ® and named Filtrete ® which has tested at 99.99% efficient in filtering airborn bacteria having diameters as low as 0.2 microns and 99.98% efficient in filtering airborn viruses having diameters as low as 0.02 microns. A proper filter thickness to achieve these efficiencies over a peripherally supported 3½" blow tube orifice is 200 gm/sq.m.

Figure 17:
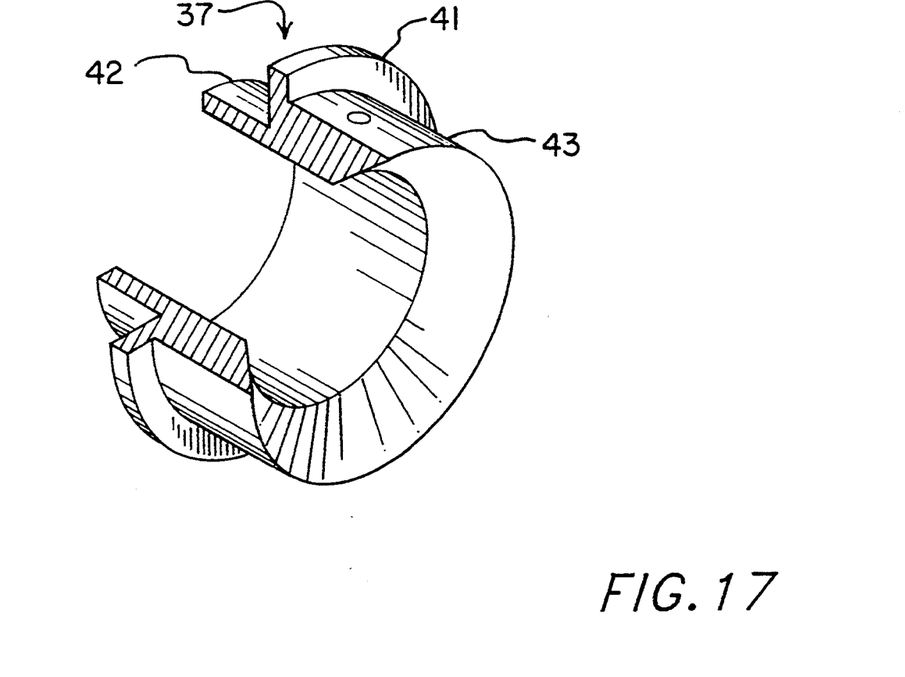
FIG. 17 is a top perspective view of spirometer coupling unit (adapter).

The bacteria filter embodiment in the prior art also consisted of a coupling device 37 shown in FIG. 17. This coupling device 37 allows the filter system to be used with spirometers having different coupling specifications. Divider 41 separates the instrument side 42 from the filter side 43. A coupling device such as that shown in FIG. 17 can also be used with the one piece disposable bacteria filter units shown in FIGS. 6, 7, 8, 9 (a),(b),(c), 10 (a),(b),(c), 11, 12, 13, 14 (a),(b),(c), 15 (a),(b),(c).

The resistance of the disposable bacteria filter assembly 38 is approximately 0.9 cm H₂O/liter/second at 12 liters per second flow. This is well below the ATS standard of 1.5 cm H₂O/liter/second at 12 liters per second flow for the overall spirometer system for low filter resistance tests such as a forced vital capacity test.

ATS standards call for a total dead space for the diffusion and residual air tests of the spirometer and filter combination of under 150 cc's.

Referring next to FIGS. 6, 7, 8, 9 (a),(b),(c), 10 (a),(b),(c), 11, 12, 13, 14 (a),(b),(c), 15 (a),(b),(c) the one piece disposable bacteria filter 40 consists of an internal filter means 20 sandwiched between the receptive housing 15 and the mouthpiece housing 16 of the one piece disposable bacteria filter 40. Parameters well within the established guidelines of the ATS are achieved in a 3½" design (FIGS. 6, 7, 8, 9 (a),(b),(c), 10 (a),(b),(c)) and a 4" design (FIGS. 11, 12, 13, 14 (a),(b),(c), 15 (a),(b),(c)).

The 3½" one piece disposable multitest bacteria filter 40 is shown in FIGS. 6, 7, 8, 9 (a),(b),(c), 10 (a),(b),(c). The two parts of the one piece disposable bacteria filter 40 are the receptive housing 15 and the mouthpiece housing 16. Fins 17, 18 are an integral part of the receptive housing 15 and the mouthpiece housing 16, respectively. The fins 17, 18 maintain the central support for the internal filter means 20, thereby meeting the required dead space without sacrificing the required resistance.

Figure 7:
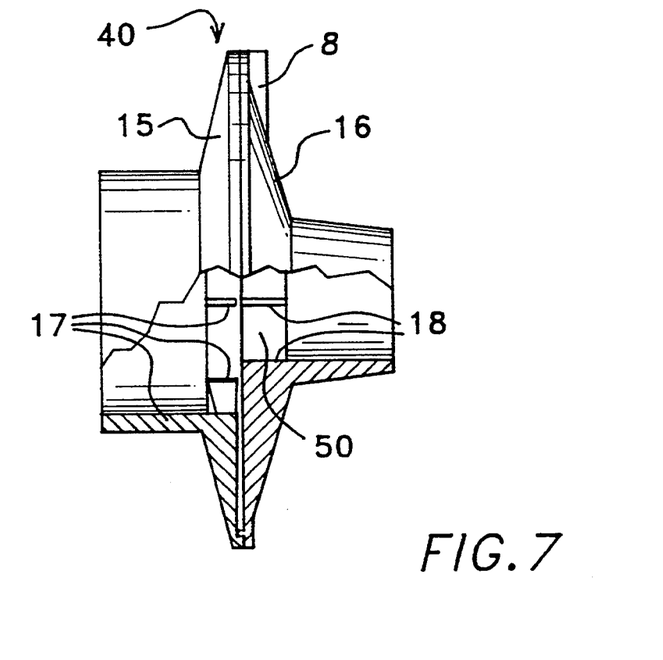
FIG. 7 is a partial cutaway view of the 3½" one piece disposable bacteria filter shown in FIG. 6.

FIG. 7 shows the fins 17, 18 in a partial cutaway view of the one piece disposable bacteria filter 40. Also shown in FIG. 7 is the dead space 50.

The adapter 37 plus dead space of the disposable bacteria filter assembly filter 40 have a total dead space of 90 cc's. This meets the standards for low dead space as required by tests such as the diffusion test and the lung volume test.

Figure 8:
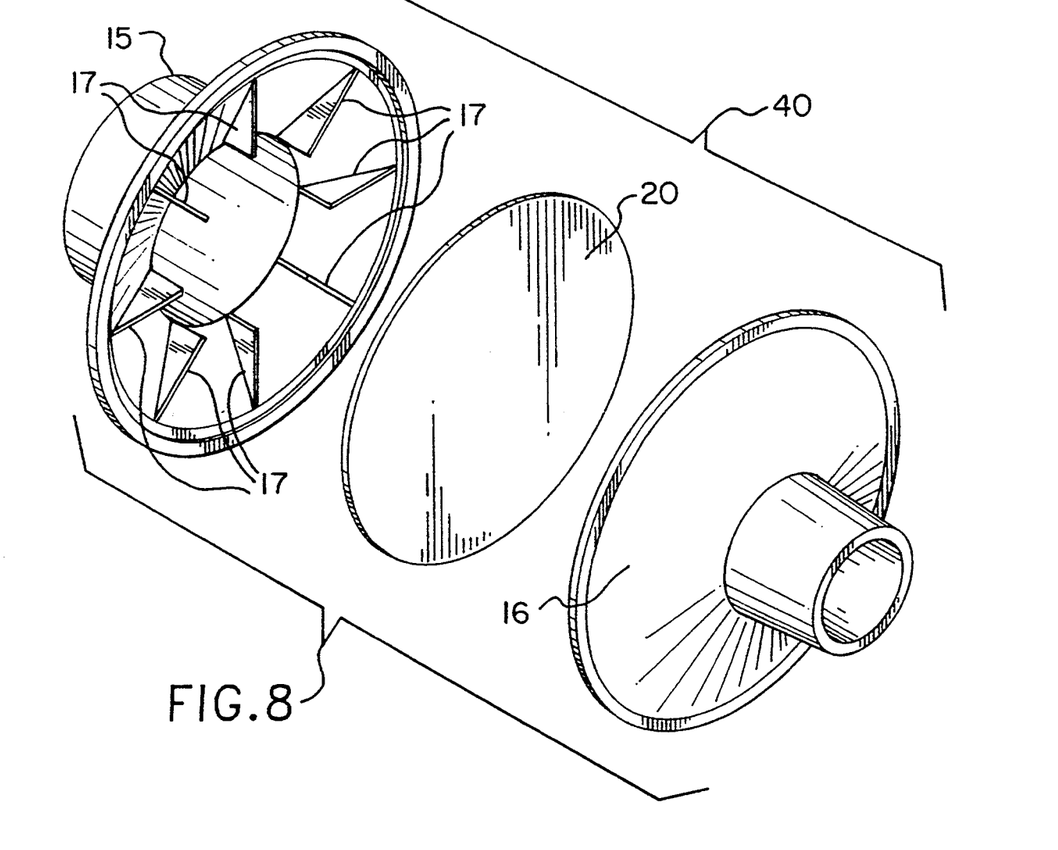
FIG. 8 is an exploded view of the 3½" one piece disposable bacteria filter shown in FIG. 6.

FIG. 8 shows an exploded view of the one piece disposable bacteria filter 40. The internal filter means 20 is supported by the fins 17 of the receptive housing 15 during exhale. The fins 18 of the mouthpiece housing 16 support the internal filter means 20 during inhalation.

Figure 9A:
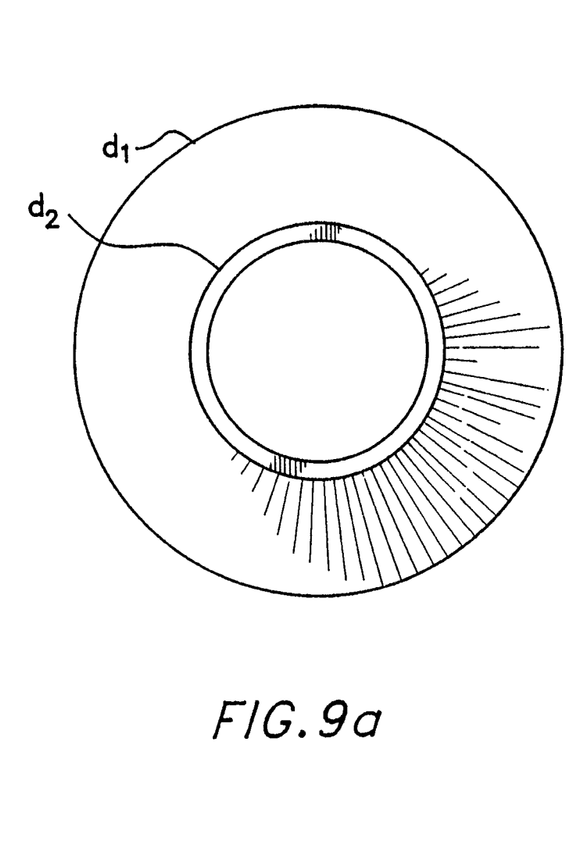
FIG. 9(a) is a back plan view of the receptive housing of the 3½" one piece disposable bacteria filter shown in FIGS. 6, 7, 8.
Figure 9B:
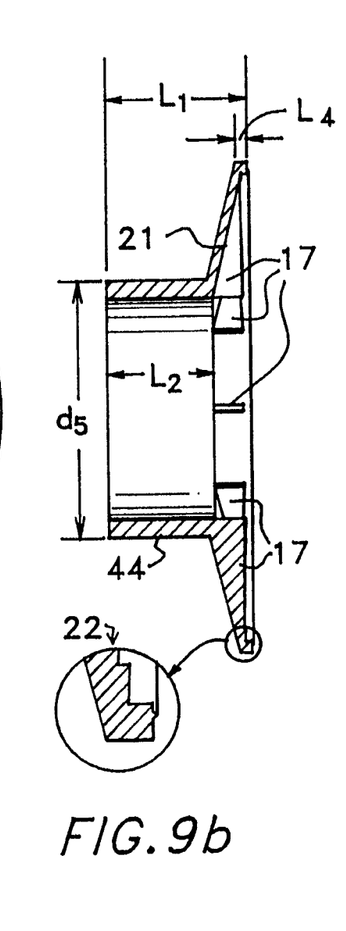
FIG. 9(b) is a cross sectional view of the receptive housing of the 3½" one piece disposable bacteria filter shown in FIGS. 6, 7, 8.
Figure 9C:
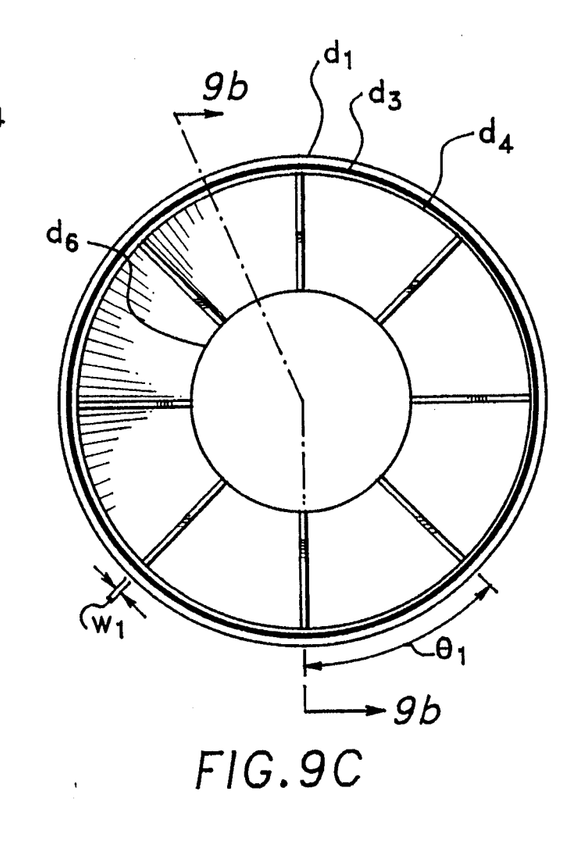
FIG. 9(c) is a front plan view of the receptive housing of the 3½" one piece disposable bacteria filter shown in FIGS. 6, 7, 8.

Details of the 3½" receptive housing 15 are shown in FIGS. 9 (a),(b),(c). Refer to the following table for dimensions.

TABLE

| FIGS. 9 (a),(b),(c) | |
| --- | --- |
| $d_1 = ⌀\ 3.70$ | $L_1 = 1.32$ |
| $d_2 = ⌀\ 2.00$ | $L_2 = .850$ |
| $d_3 = ⌀\ 3.465$ | $L_4 = .310$ |
| $d_4 = ⌀\ 3.26$ | $\Theta_1 = 45°$ |
| $d_5 = ⌀\ 1.79$ | $W_1 = 8 \times .050$ |
| $d_6 = ⌀\ 1.72$ | |

Figure 18:
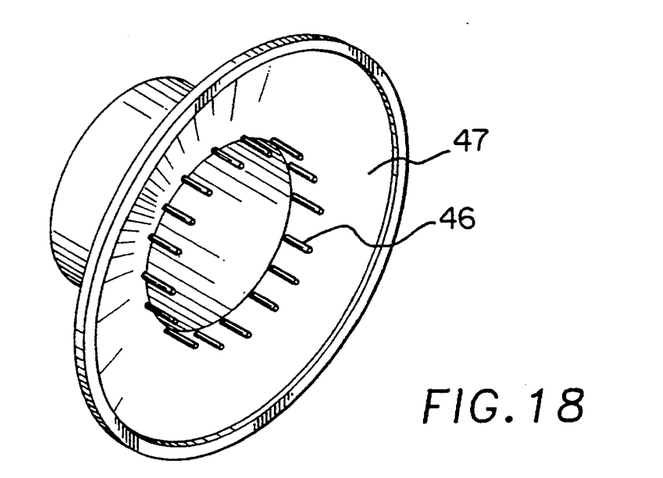
FIG. 18 is a side perspective view of a receptive housing with posts.
Figure 19:
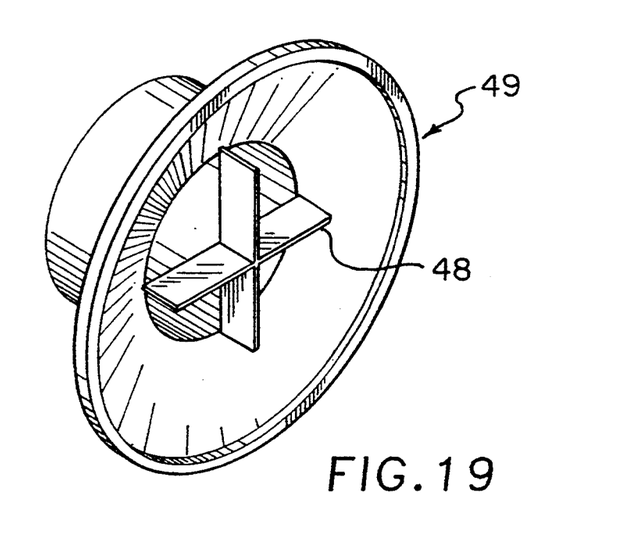
FIG. 19 is a side perspective view of a receptive housing with crosshairs.

The edge 22 of the receptive housing 15 provides peripheral support for the internal filter means 20. Eight fins 17 provide central support for the internal filter means 20. These eight fins 17 are equally spaced. Central support could alternately be provided by a series of posts, posts and fins, crosshairs, or "S" shaped prongs as shown in FIGS. 18, 19. FIG. 18 shows receptive housing 47 having posts 46. A mouthpiece housing (not shown) would have matching posts. FIG. 19 shows a receptive housing 49 having crosshairs 48. A mouthpiece housing (not shown) would have matching crosshairs.

Figure 10A:
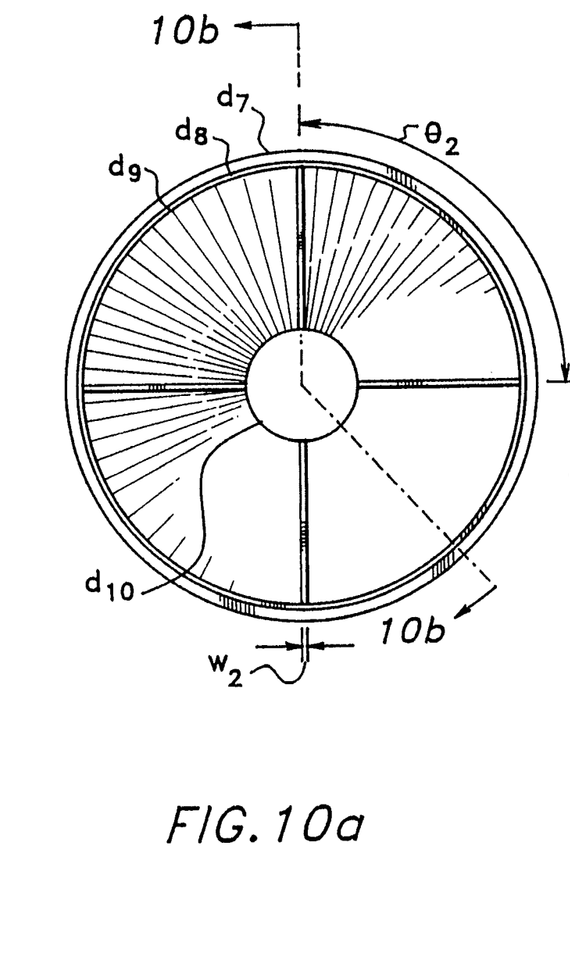
FIG. 10(a) is a front plan view of the mouthpiece housing of the 3½" one piece disposable bacteria filter shown in FIGS. 6, 7, 8.
Figure 10B:
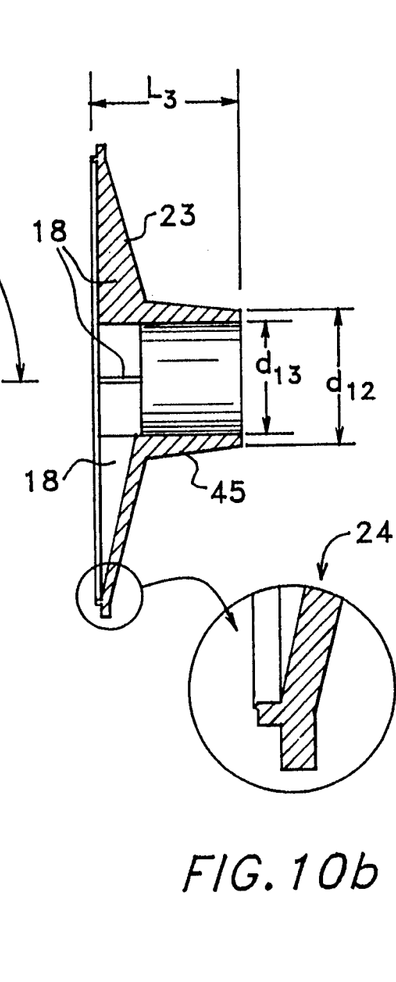
FIG. 10(b) is the cross sectional view of the mouthpiece housing of the 3½" one piece disposable bacteria filter shown in FIGS. 6, 7, 8.
Figure 10C:
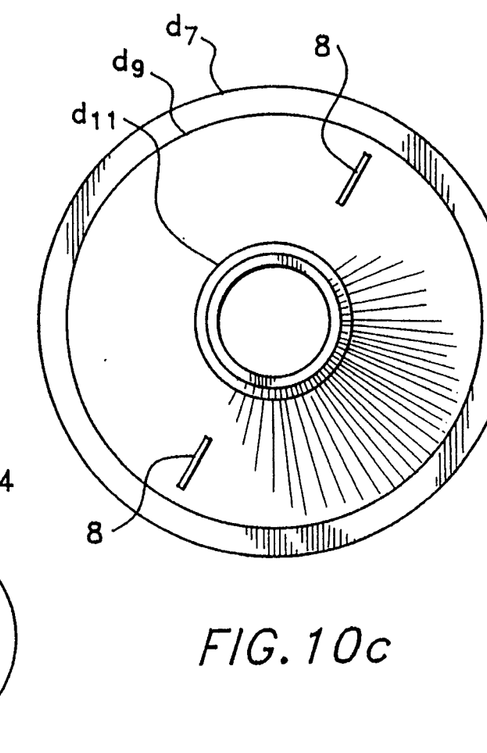
FIG. 10(c) is the back plan view of the mouthpiece housing of the 3½" one piece disposable bacteria filter shown in FIGS. 6, 7, 8.

FIGS. 10 (a),(b),(c) show details of the 3½" mouthpiece housing 16. Refer to the following table for dimensions

TABLE

| FIGS. 10 (a),(b),(c) | |
| --- | --- |
| $d_7 = ⌀\ 3.72$ | $d_{12} = ⌀\ 1.125$ |
| $d_8 = ⌀\ 3.455$ | $d_{13} = ⌀\ 1.015$ |
| $d_9 = ⌀\ 3.30$ | $L_3 = 1.72$ |
| $d_{10} = ⌀\ 0.980$ | $\Theta_2 = 90°$ |
| $d_{11} = ⌀\ 1.240$ | $W_2 = 4 \times .050$ |

The mouthpiece housing 16 has four fins 18 to provide central support for the internal filter means 20. Peripheral support is provided for the internal filter means 20 by the snap together edge 24 of the mouthpiece housing 16.

Finger tabs 8 are optionally provided on the mouthpiece to aid in the mounting of the one piece disposable bacteria filter 40. Edge 22 of the receptive housing 15 provides peripheral supports for the filter means 20 by snapping together with edge 24 of the mouthpiece housing 16. This edge joint assembly of 22, 24 is permanently sealed (i.e., with adhesive or ultrasonic weld) to form an air tight circular joint.

The 3½" one piece disposable bacteria filter 40 provides low filter resistance of 0.6 cm H₂O/liter/second at a flow rate of 12 liters per second. The fins, or other integral support means, allow for a 70 cc dead space 50 for the one piece disposable bacteria filter 40.

FIGS. 11, 12, 13, 14 (a),(b),(c), 15 (a),(b),(c) show a 4" one piece disposable bacteria filter 51.

Figure 11:
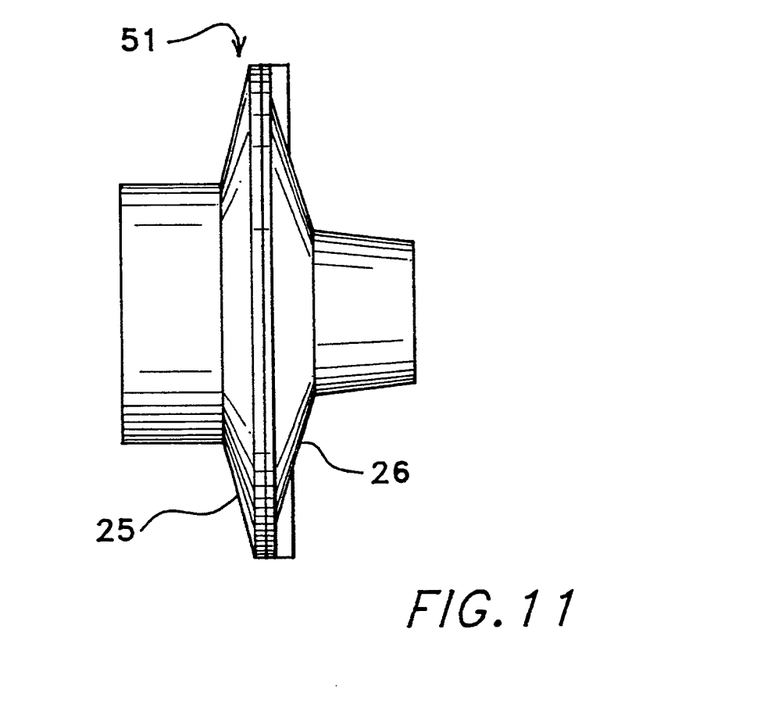
FIG. 11 is a side plan view of a 4" one piece disposable bacteria filter.

The 4" one piece disposable bacteria filter 51 is shown in FIG. 11. The two parts of the housing unit 51 are the receptive housing 25 and the mouthpiece housing 26. Fins 27, 28 are an integral part of the housing units to maintain the required dead space 53 without sacrificing the required resistance.

Figure 12:
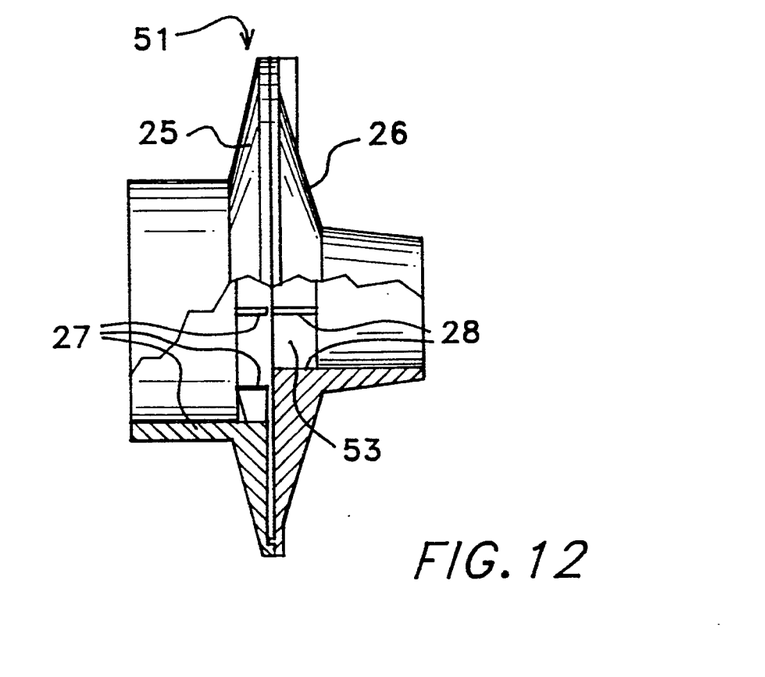
FIG. 12 is a partial cutaway view of the 4" one piece disposable bacteria filter shown in FIG. 11.

FIG. 12 shows the fins 27, 28 in a partial cutaway of the one piece disposable bacteria filter 51.

Figure 13:
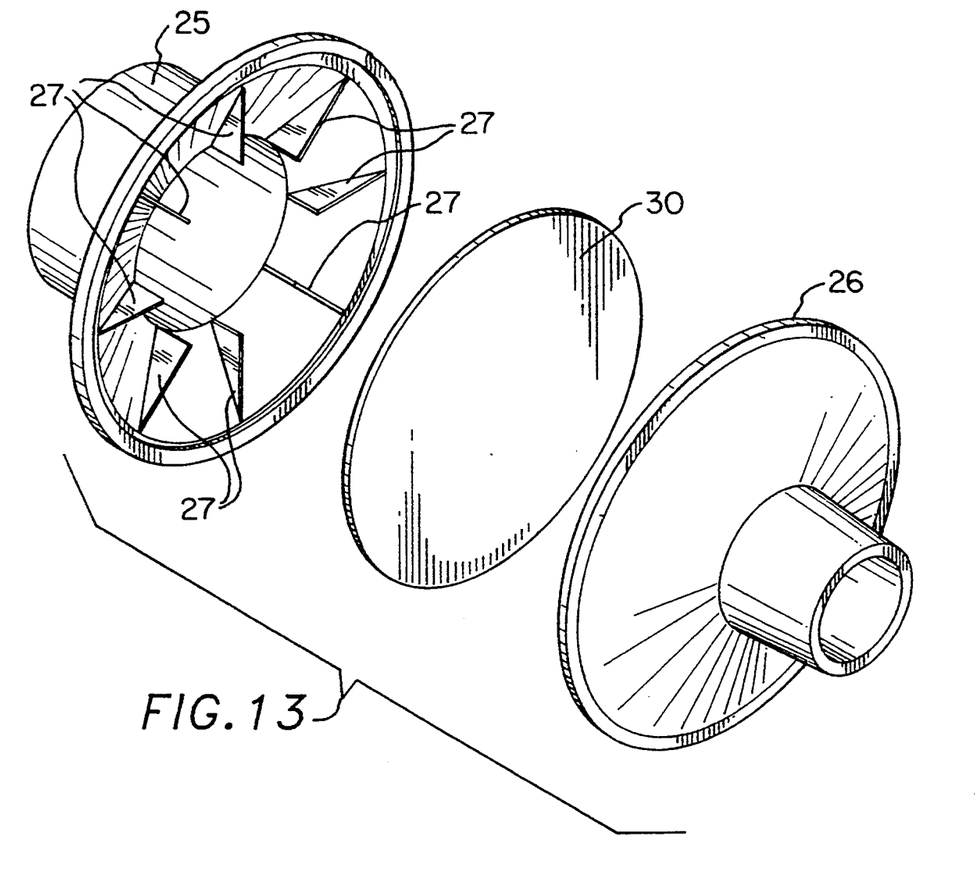
FIG. 13 is an exploded view of the 4" one piece disposable bacteria filter shown in FIG. 11.

FIG. 13 shows an exploded view of the one piece disposable bacteria filter 51. The internal filter means 30 is supported by the fins 27 of the receptive housing 25 during exhale. The fins 28 of the mouthpiece housing 26 support the internal filter means 30 during inhalation.

Figure 14A:
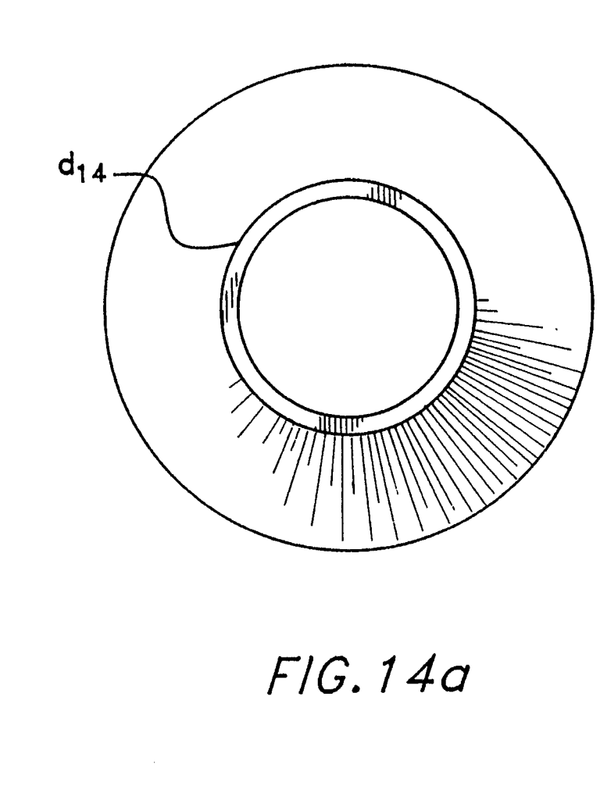
FIG. 14(a) is a back plan view of the receptive housing of the 4" one piece disposable bacteria filter shown in FIGS. 11, 12, 13.
Figure 14B:
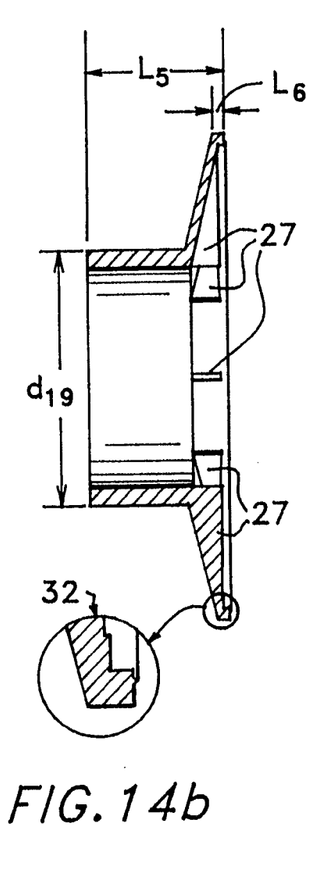
FIG. 14(b) is a cross sectional view of the receptive housing of the 4" one piece disposable bacteria filter shown in FIGS. 11, 12, 13.
Figure 14C:
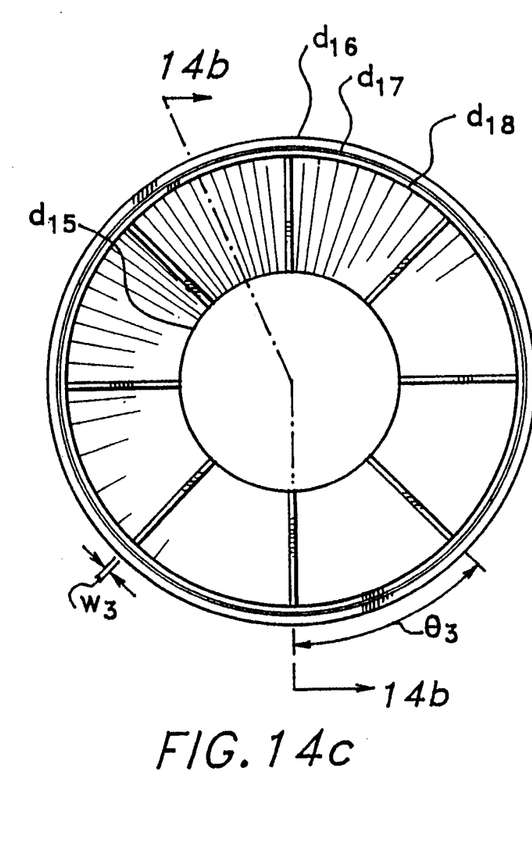
FIG. 14(c) is a front plan view of the receptive housing of the 4" one piece disposable bacteria filter shown in FIGS. 11, 12, 13.

Details of the 4" receptive housing 25 are shown in FIGS. 14 (a),(b),(c). The edge 32 of the receptive housing 25 provides peripheral support for the filter means 30. Eight fins 27 provide central support for the filter means 30. These eight fins 27 are equally spaced. Central support could alternately be provided by a series of posts, posts and fins, or crosshairs, as shown in FIGS. 18, 19.

Figure 15A:
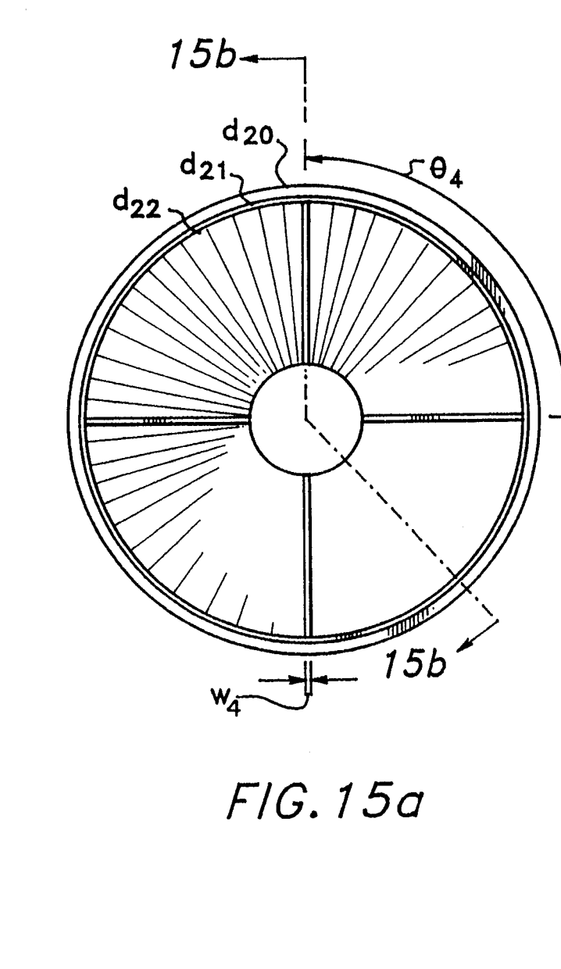
FIG. 15(a) is a front plan view of the mouthpiece housing of the 4" one piece disposable bacteria filter shown in FIGS. 11, 12, 13.
Figure 15B:
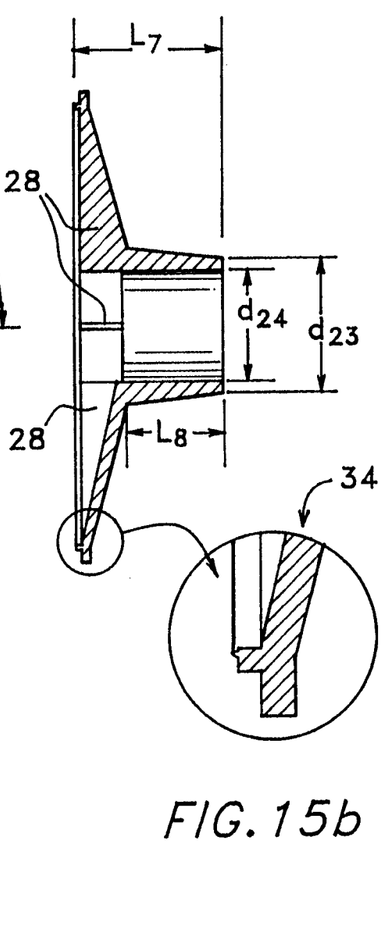
FIG. 15(b) is the cross sectional view of the mouthpiece housing of the 4" one piece disposable bacteria filter shown in FIGS. 11, 12, 13.
Figure 15C:
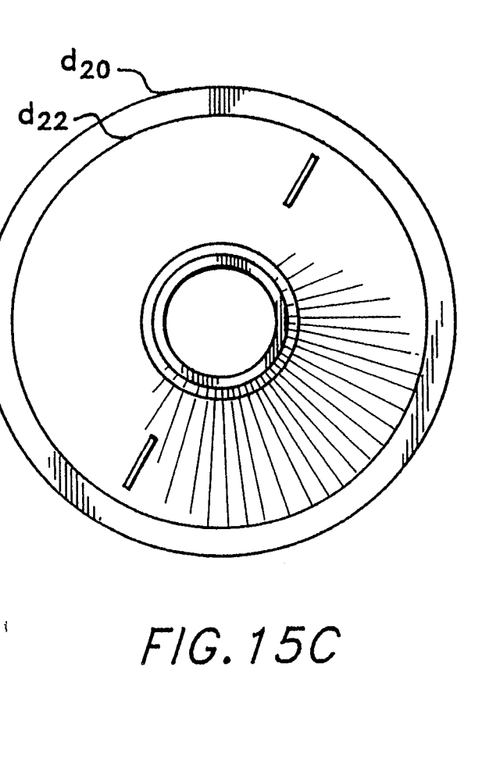
FIG. 15(c) is the back plan view of the mouthpiece housing of the 4" one piece disposable bacteria filter shown in FIGS. 11, 12, 13.

FIGS. 15 (a),(b),(c) show details of the 4" mouthpiece housing 26. The mouthpiece housing 26 has four fins 28 to provide central support for the internal filter means 30. Peripheral support is provided for the internal filter means 30 by the snap together edge 34 of the mouthpiece housing 26.

Edge 32 of the receptive housing 25 provides peripheral support for the filter means 30 by snapping together with edge 34 of the mouthpiece housing 26. This edge joint assembly of 32, 34 is permanently sealed (i.e., with adhesive or ultrasonic weld) to form an air tight circular joint.

The 4" one piece disposable bacteria filter 51 provides an even lower resistance of 0.45 cm $H_2O$/liter/second at a flow rate of 12 liters per second. The fins or other integral support means allow for a 70 cc dead space.

The dimensions of the 4" one piece disposable bacteria filter 51 are provided in the tables below.

TABLE

| FIGS. 14 (a),(b),(c) | |
|---|---|
| $d_{14} = \varnothing\ 2.00$ | $d_{19} = \varnothing\ 1.79$ |
| $d_{15} = \varnothing\ 1.72$ | $L_5 = 1.145$ |
| $d_{16} = \varnothing\ 4.25$ | $L_6 = .125$ |
| $d_{17} = \varnothing\ 4.00$ | $\Theta_3 = 45°$ |
| $d_{18} = \varnothing\ 3.75$ | $W_3 = 8 \times .050$ |
| FIGS. 15 (a),(b),(c) | |
| $d_{20} = \varnothing\ 4.25$ | $L_7 = 1.265$ |
| $d_{21} = \varnothing\ 3.985$ | $L_8 = .816$ |
| $d_{22} = \varnothing\ 3.920$ | $\Theta_4 = 90°$ |
| $d_{23} = \varnothing\ 1.125$ | $W_4 = 4 \times .050$ |
| $d_{24} = \varnothing\ 1.015$ | |

Figure 16:
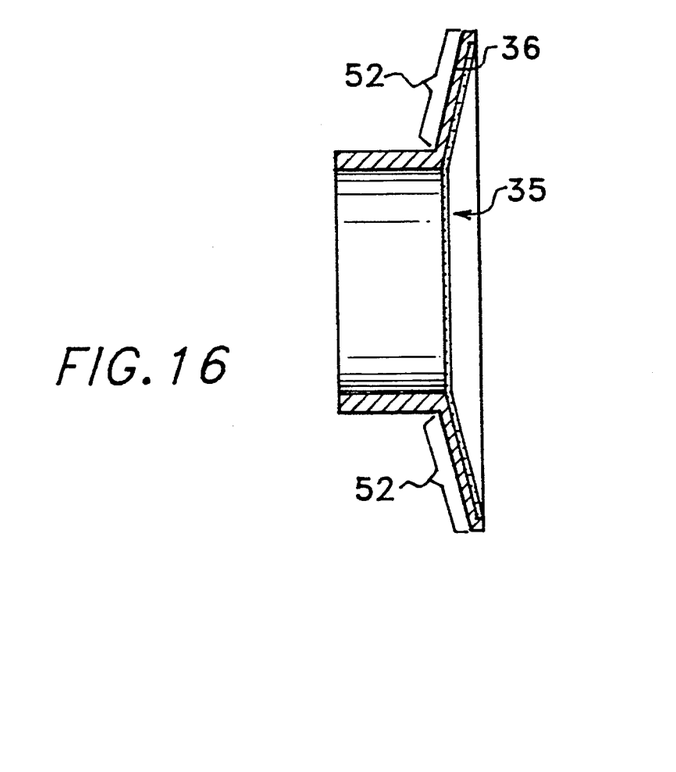
FIG. 16 is a cross sectional view of a filter means in contact with a receptive housing.

The fins 17, 18 of the 3½" embodiment and 27, 28 of the 4" embodiment are an integral part of the design. These are required to meet the performance criteria. Without these fins or other means of support the filter means will come in contact with the housing unit as shown in FIG. 16. When the filter means 35 comes in contact with the housing unit 36 the surface contact area of the filter means 35 is reduced by the area 52. The prior art avoided contact area by increasing the dead space. The present invention avoids increasing the dead space by means of the central support for the filter means.

The filter means 20, 30 are preferably a 3M ® Filtrete ® filter having a density of 150 gm/sq.m. or less.

KEY

1. Receptive housing of deep design disposable bacteria filter (prior art)
2. Mouthpiece housing of deep design disposable bacteria filter (prior art)
5. Disposable filter paid
6. O ring
7. Recessed groove in housing for receiving O ring
8, 800 Finger tabs
9. Receptive housing flange
10. Dead space
11. Female threads on receptive housing
13. Mouthpiece housing flange
14. Male threads on mouthpiece housing
15. Receptive housing of 3½" one piece disposable bacteria filter.
17. Fins on 3½" receptive housing
18. Fins on 3½" mouthpiece housing
20. Disposable filter pad for 3½" one piece disposable bacteria filter
21. 3½" receptive housing flange; one piece
22. One piece edge on 3½" receptive housing
24. One piece edge on 3½" mouthpiece housing
25. Receptive housing of 4" one piece disposable bacteria filter
26. Mouthpiece housing of 4" one piece disposable bacteria filter
27. Fins on 4" receptive housing
28. Fins on 4" mouthpiece housing
30. Disposable filter pad for 4" one piece disposable bacteria filter
32. Edge on 4" receptive housing flange
34. Edge on 4" mouthpiece housing
35. Filter means in contact with housing unit
36. Housing unit with filter means in contact Adapter/spirometer coupler
37. Adapter/spirometer coupler
38. Low filter resistance high dead space design
39. High filter resistance low dead space design
40. 3½" one piece disposable bacteria filter
41. Divider
42. Instrument side
43. Filter side
44. Connecting members
45. Connecting members
46. Posts
47. Receptive housing with posts
48. Crosshairs
49. Receptive housing with crosshairs
50. Dead air space
51. 4" one piece disposable bacteria filter
52. Contact area between filter means and housing
53. Dead air space Although the present invention has been described with reference to preferred embodiments, numerous modifications and variations can be made and still the result will come within the scope of the invention. No limitation with respect to the specific embodiments disclosed herein is intended or should be inferred.

I claim:

1. A one piece disposable bacteria filter comprising:
a unitary housing having a distal mouthpiece and a proximal mounting member;
said unitary housing further comprising an outside diameter;
an internal filter means functioning to collect bacteria;
said internal filter means further comprising a density;
peripheral support means for said internal filter means;
central support means for said internal filter means; and
said one piece disposable bacteria filter having an airflow resistance of 0.6 cm $H_2O$/liter/second or less at 12 liters per second flow, and a dead space of about 70 cc or less.

2. The filter of claim 1 wherein said outside diameter is 3.5 inches.

3. The filter of claim 1 further comprising an adapter having a divider separating a lung testing instrument from the proximal mounting member.

4. The filter of claim 1 wherein said internal filter means further comprises a gauze filter.

5. The filter of claim 3 wherein said density further comprises 150 gm/sq. m or less.

6. The filter of claim 1 wherein said peripheral support means further comprises said unitary housing having a first half and second half construction with a joint therebetween which supports the periphery of said internal filter means.

7. The filter of claim 6 wherein said central support means further comprises posts emanating from each half from the periphery toward the center of the said internal filter and supporting the said internal filter therebetween.

8. The filter of claim 5 wherein said central support means further comprises a pair of crosshair projections, the first member emanating from the mouthpiece and the second member emanating from the mounting member, and the pair sandwiching the said internal filter therebetween.

9. The filter of claim 6 wherein said central support means further comprises straight fins emanating from each half from the periphery toward the center of the said internal filter means and supporting the said internal filter therebetween.

10. A one piece disposable bacteria tiller comprising:
a unitary housing having a distal mouthpiece and a proximal mounting member;
said one piece housing further comprising an outside diameter;
an internal filter means functioning to collect bacteria;
said internal filter means further comprising a density;
peripheral support means for said internal filter means;
central support means for said internal filter means; and
said one piece disposable bacteria filter having an airflow resistance of 0.45 cm $H_2O$/liter/second or less at 12 liters per second flow, and a dead space of about 70 cc or less.

11. The filter of claim 10 wherein said outside diameter is 4.0 inches.

12. The filter of claim 10 further comprising an adapter having a divider separating a lung testing instrument from the proximal mounting member.

13. The filter of claim 10 wherein said internal filter means further comprises a gauze filter.

14. The filter of claim 13 wherein said density further comprises 150 gm/sq. m or less 15. The filter of claim 10 wherein said peripheral support means further comprises said unitary housing having a first half and second half construction with a joint therebetween which supports the periphery of the said internal filter.

16. The filter of claim 15 wherein said central support means further comprises a pair of crosshair projections, the first member emanating from the mouthpiece and the second member emanating from the mounting member, and the pair supporting the said internal filter therebetween.

17. The filter of claim 15 wherein said central support means further comprises fins emanating from each half from the periphery toward the center of the said internal filter and supporting the said filter means therebetween.

18. The filter of claim 15 wherein said central support means further comprises posts emanating from each half from the periphery toward the center of the said internal filter means and supporting the said internal filter therebetween.

* * * * *